United States Patent [19]
Draenert

[11] Patent Number: 5,374,121
[45] Date of Patent: Dec. 20, 1994

[54] MIXING APPARATUS WITH MIXING ROD SUPPORTING LID

[76] Inventor: Klaus Draenert, Gabriel-Max-Str. 3, 8000 Munich 90, Germany

[21] Appl. No.: 730,501

[22] Filed: Jul. 11, 1991

Related U.S. Application Data

[63] Continuation of Ser. No. 302,689, Jan. 23, 1989, abandoned.

[30] Foreign Application Priority Data

May 21, 1987 [DE] Germany ............................. 3717134

[51] Int. Cl.$^5$ .......................... B01F 15/00; B01F 3/08
[52] U.S. Cl. .................................... 366/242; 366/139; 366/241; 366/255; 366/348; 366/347; 366/65; 215/316; 215/321; 220/200; 220/DIG. 19
[58] Field of Search ............... 366/242, 139, 241, 255, 366/348, 349, 275, 341, 347, 154, 64, 65, 261, 255; 220/287, 200, DIG. 19; 215/307, 321, 316, 317

[56] References Cited

U.S. PATENT DOCUMENTS

| | | | |
|---|---|---|---|
| 1,412,401 | 4/1922 | Gotfredsen | 366/251 |
| 2,765,832 | 10/1956 | Tupper | 366/341 |
| 3,357,429 | 11/1964 | Folkman et al. | 215/307 |
| 3,430,826 | 3/1969 | Microulis | 215/321 |
| 4,561,782 | 12/1985 | Jacobsen et al. | 366/349 |
| 4,758,096 | 7/1988 | Gunnarsson | 366/139 |

FOREIGN PATENT DOCUMENTS 1057752  5/1959  Germany .

Primary Examiner—Timothy F. Simone
Assistant Examiner—Gary K. Graham
Attorney, Agent, or Firm—Kinney & Lange

[57] ABSTRACT

The invention relates to a mixing apparatus comprising a mixing bowl and a lid for vacuum-sealing the mixing bowl, which lid is provided with a passage for a mixing rod. The lid is relatively rigid in the axial direction of the mixing bowl, whereas at least the portion of the lid which surrounds the passage is radially movable.

10 Claims, 4 Drawing Sheets

MIXING APPARATUS WITH MIXING ROD SUPPORTING LID

This is a continuation of application Ser. No. 07/302,689 filed on Jan. 23, 1989, abandoned as of the date of this application.

BACKGROUND OF THE INVENTION

The invention relates to an apparatus for stirring substances and for mixing a compound or a mixture of substances comprising at least two components. In particular, the invention relates to an apparatus for mixing bone cement and filling it into an applicator.

The term "mixing" is generally understood to mean the introduction of the parts of one substance into the parts of other substances. The aim is to obtain as homogenous as possible a distribution of the various components of the mixture, for instance to initiate or promote a chemical reaction between the components such as the following polymerisation of a two-component or multi-component mixture.

Various kinds of mixing processes and mixing devices are known. The process of mixing can be carried out by stirring, mingling, rolling, kneading, emulsifying, suspending, dissolving or by means of ultrasonic waves.

The known mixing processes and mixing apparatus, however, have the disadvantage that impurities, such as air, can enter into the mixing system and that the gas enclosures or occlusions already contained at the beginning of the mixing process in the substances to be mixed and those which form during the actual process of mixing, for instance via a chemical reaction, cannot be removed from the mixing system. A further disadvantage which often occurs is that the mixing vessel is not identical to the vessel in which the mixed compound is to be further processed. It then becomes necessary to transfer the compound. The transferral of the mixed compound might cause problems, especially if reactions such as polymerization occur in the compound.

Further, specific problems arise in the processing and mixing of bone cement and when filling the same into the vessel from which the bone cement is later applied.

The bone cement is usually made of cold-curing two-component resins which anchor the components of artificial joints into the bony bed. The bone cement hardens as soon as it has been applied. Due to its plastic properties, it anchors the components of the prosthesis into the bony bed by interlocking. Polymethylmethacrylates (PMMA) have been used as bone cement for several years now. They comprise a powdery bead polymer which is superficially dissolved in a liquid monomer and is then embedded by the polymerisation of said liquid monomer. In the mixing phase, the monomer surrounds the usually globular polymer powder. This firstly leads to a suspension of the globules in which a considerable amount of air bubbles are entrapped. The process of polymerisation occurs exothermically. In addition to the entrapped air bubbles, when the polymer globules are surrounded by the monomer, so-called "lee phenomena" regularly appear; this means sites where the polymer globules have not been sufficiently wetted. In addition, the monomeric liquid evaporates during the process of exothermal polymerisation which leads to the fact that in the end the hardened bone cement is riddled with bubbles of various ethiology and genesis.

As a rule, the polymer powder is added to the monomer and then mixed in a bowl using a spatula. In the processing phase which follows the mixing phase, the bone cement is applied to the bony bed either manually, which is usually the case, or sometimes with a syringe. To date there are hardly any publications that deal with the mixing phase and bloating phase of the bone cement and with the artefact-free insertion thereof into the syringe system.

The further processing of the bone cement stirred in the mixing bowl in the above-mentioned fashion depends on its viscosity. Bone cement of a very low viscosity can be poured from the bowl into the cartridge of the bone cement syringe; the problem, however, is that the stream of bone cement flowing into the syringe can be very easily diverted, for instance via electrostatic charging, so that the walls of the cartridge and the opening thereof are almost always covered with bone cement. Highly viscous bone cement cannot be poured at all. It has to be removed and kneaded by hand in order to press out the largest of the air enclosures. The bone cement is then rolled into a sausage-shaped mass which can be inserted into the cartridge. When manually processing the cement, not only does one have to wait until the bone cement no longer sticks to the surgical gloves, but the cement mixture also remains unprocessed in the most important stage of the bloating or swelling phase and the pre-polymerisation phase that follows.

The known attempts to try and solve the problem of mixing the cement in a so-called "closed system" have not managed to produce a mixture better than that produced by hand.

SUMMARY OF THE INVENTION

Hence the object of the invention is to provide an apparatus with which a mixture of substances comprising at least two components can easily, rapidly and without bubbles be mixed and introduced into the vessel in which the further processing of the mixture is to take place.

A further object of the invention is to provide a device for mixing bone cement and filling it into an applicator with which apparatus bone cement consisting of several components can easily, rapidly, without bubbles and without being touched by the surgeon be mixed and filled into an applicator from which the bone cement is to be applied to the bony bed.

Yet a further object of the invention is to provide an evacuable mixing apparatus for stirring and mixing substances without leaving bubbles.

These objects are achieved by the features of the patent claims.

According to the invention, the substances to be mixed, preferably a curable two-component system such as a mixture of polymer powder and monomer, are pushed through an opening or taper out of a mixing bowl into the applicator after having been mixed in said mixing bowl. This process is called "extrusion mixing".

The mixing bowl or mixing vessel is preferably cylindrical with one closed and one open end. The applicator vessel in which the compound is further processed once it has been intermixed or blended, is preferably cylindrical, too, and has one open end. The other end of the applicator vessel or the second vessel can be closed by means of a cap or plunger. The outer perimeter of the second vessel is provided with a sealing means, preferably at the open end thereof, the sealing means preferably comprising several flexible discs or lamellae.

In order to mix and transfer the mixture of substances, the second cylindrical vessel or hollow member is axially pushed with its open end first into the first vessel which contains the substances to be mixed or which have already been partially mixed. By means of this relative motion of the two vessels, the mixture is forced through the opening into the second vessel as the sealing means seals off the space between the inner wall of the mixing vessel and the outer wall of the second vessel in such a manner that only gas can escape between them, but not the substances to be mixed.

When applying the above principle to mixing bone cement and filling it into an applicator, the monomer is firstly placed into a mixing bowl or cup whereupon the polymer powder is added to the formulation and is mixed and stirred under vacuum, as will be explained in detail. Instead of removing all of the cement paste with the spatula, or pouring it out if the cement has a low viscosity, as in conventional processes, the cartridge-shaped applicator with its mounted sealing means is inserted through the opening of the mixing bowl. If the sealing means is provided as a cylindrical member with a central, tubular opening and several disc-shaped lamellae, said means can be mounted to any kind of commercially available cartridge by means of adapters, preferably small rings, and can be used in combination with these cartridges. The cylindrical vessel described in EP-A1-170 120 is the one preferably used as the applicator or cartridge. By pushing in the cartridge and the sealing means coupled thereto, the cement which has been pre-mixed with the spatula is forced into the cartridge through the central opening of the sealing means. The diameter of the opening can be either the same or smaller than that of the cartridge. The extruding effect leads to a more thorough mixing of the bone cement, and it proceeds from the mixing bowl into the cartridge without having been touched by the surgeon's hands. Furthermore, the flowing process presses out large air bubbles.

According to the invention, instead of using a conventional spatula to premix the cement, a mixing apparatus is used which preferably comprises a round rod advantageously coated with teflon. The round rod has the advantage that it does not rupture the mixture, but promotes the blending thereof by means of a laminar flow of the layers of the mixture. Furthermore, when mixing the bone cement and removing the rod, almost no cement sticks to the teflon-coated round rod.

In order to avoid air enclosures, the mixing of the components, for example the components of the bone cement, is carried out under vacuum. For this, the mixing vessel preferably has a surface ground upper rim onto which a lid or cap is mounted. The mixing vessel can be sealingly connected with the lid by means of a sealing ring covered with vacuum grease or by means of a silicon coating. The lid can also be connected to the mixing vessel in a vacuum-tight manner by means of an easily removable flanged joint. The lid has a connecting means for a tube feed to which a vacuum pump is attached.

According to the invention, the lid of the mixing bowl is formed thus that it essentially stays in shape and is not, for instance, dragged into the mixing bowl when under partial vacuum, i.e. when the mixing bowl is being evacuated. At the same time said lid is flexible enough for the mixing rod, which is inserted through a feed-through or passage in the lid in a vacuum-tight manner, to be movable or mobile in the radial direction of the mixing bowl so that it is possible to carry out a stirring movement with the mixing rod in the evacuated mixing bowl. The lid is preferably flexible enough to allow the mixing rod to be led along and parallel to the entire inner wall of the mixing bowl, but at least along its bottom inner rim. In the axial direction, however, the lid must be stiff enough to prevent it from being crushed or pulled into the mixing bowl during evacuation.

The lid preferably has a firm rim which is placed onto the rim of the mixing vessel, and a feed-through or passage for the round rod used in the mixing process. The sealed feed-through for the round rod is preferably arranged within an inner portion of the lid, said inner portion being made of flexible material or flexibly shaped in another manner, and the lid being connected in a vacuum-tight fashion, preferably integrally, to the firm rim. The inner portion of the lid can be tent-like and can have at its upper end the feed-through or passage which is shaped as an annular guiding means and is preferably made of rubber or silicon, through which the round rod is fed and which holds said round rod in a vacuum-tight manner. As the inner portion of the lid is flexible, the round rod can be moved or is mobile in a radial direction within the mixing vessel and can be guided along the inner wall of the mixing vessel so that none of the components to be mixed, for instance no bone cement powder, remains on the inner wall untouched. This is of extraordinary significance for obtaining thorough mixing. In this embodiment, the material the lid is made of must be stiff enough to withstand completely collapsing when under partial vacuum.

In a further preferred embodiment, the lid is integrally shaped in the form of bellows which taper as they go up, i.e. away from the mixing bowl. The bellow-shaped lid preferably consists of several, preferably three to five, cylindrical portions which essentially extend in the axial direction. The diameter of the portions decreases from portion to portion, and they are each connected by means of an arched transition piece. The transition pieces can be less thick than the axial portions. The bottommost portion of the lid can be thicker and thus stiffer than the other portions and can form the rim located on the upper rim of the mixing bowl. The rim of the lid preferably encompasses the rim of the mixing bowl in the form of an undercut and in such a manner that the lid is mounted on the mixing bowl in a vacuum-tight and essentially rigid, non-displacable manner. The inner diameter of the uppermost portion of the lid forms the feed-through for the mixing rod.

By mixing the bone cement under vacuum, the number of bubbles in the cement can be diminished even further and the mixture can be stirred without almost no bubble formation.

Experiments have shown that tall mixing vessels enable a much quicker and more homogenous mixing of the cement paste than wide, shallow mixing bowls or dishes which exhibit dead corners. The inner bottom of the mixing vessel is preferably spherical or concave. When the cartridge is pressed in, the first, flexible lamella of the sealing means adapts itself to the shape of the bottom of the mixing bowl in such a manner that no substance remains in the mixing bowl. It is of particular advantage if the bottom of the mixing bowl is flexible, too, so that the complete adaption of the two forms is assured.

The formation of dead spaces at the upper edge of the cement paste during the flowing process can be avoided if the foremost lamella of the sealing means is also slightly bent or concave so that the cement paste is forced radially from the outer wall of the mixing bowl to its centre.

When the cartridge with the sealing means is being pushed in, as explained above, both air and the gases released during the process of polymerisation can pass the lamallae of the sealing means and escape. The body of the sealing means can additionally comprise at least one valve through which the gases can escape.

Furthermore, during the mixing phase it is also possible to apply a vacuum and to evacuate air from the mixing bowl by applying pressure and closing the central opening or the end of the cartridge while mechanically compressing the cement at the same time. The result is that the majority of the small air bubbles, too, can be removed from the cement as early as in the mixing stage.

When filling the cement into the cartridge it is important that the end facing away from the mixing bowl is not closed or, if the cartridge has a cap, that said cap is only loosely mounted to allow the air which is pushed out in front of the cement to escape from the cartridge.

In the system described above, which is called the "half closed system", the second vessel can be a cartridge as used in the bone cement syringe according to EP-A1-170 120 or in similar syringes. In this system, the cement does not have to be touched by the surgeon's or scrub-nurse's hands or surgical gloves prior to its application, which is of great advantage. On the one hand it is a known fact that the monomer can easily penetrate the rubber gloves of the operating team, and more and more allergies to the plastic they are made of have recently become known; on the other hand, the contact-free procedure leads to a considerable reduction in the number of flaws in the cement, and it proceeds more quickly and at an earlier stage into the bone cement pistol for precompression because one does not have to wait for it to set.

The first vessel (mixing bowl) and the second vessel (applicator) are preferably made of the same material. They can be made of plastic, preferably a thermoplastic material such as a polyolefin. The use of poly(4-methyl-1-pentene) or TPX ® is particularly preferred. It is also possible to use polycarbonate.

The vacuum lid for the mixing vessel is preferably made of a sterilisable material which is essentially resistant to solvents, microorganisms and the same.

In the tent-like embodiment, the vacuum lid for the mixing vessel is preferably made of teflon or of the material used for the mixing vessel and the applicator, for instance poly(4-methyl-1-pentene).

If the vacuum lid is bellow-shaped, it is preferably made of an elastomer such as a polyester elastomer, polychloroprene rubber, polyethylene, butyl rubber (JJR), nitrile rubber (NBR), a butadiene copolymer, styrene-butadiene rubber (SBR), acrylic rubber, a fluoric elastomer, a polyolefine or silicon rubber such as Santoprene ®. The use of Hytrel ® is particularly preferred. Hytrel ® is a polyester elastomer and a block polymer made of polyethylene terephthalate and polyalkene glycol and has a molecular weight of up to 25,000.

BRIEF DESCRIPTION OF THE DRAWINGS

In the following the invention will be explained in greater depth using examples relating to mixing bone cement and filling it into an applicator, and using illustrations. The figures show.

DETAILED DESCRIPTION OF THE PREFERRED EMBODIMENT

Figure 1:
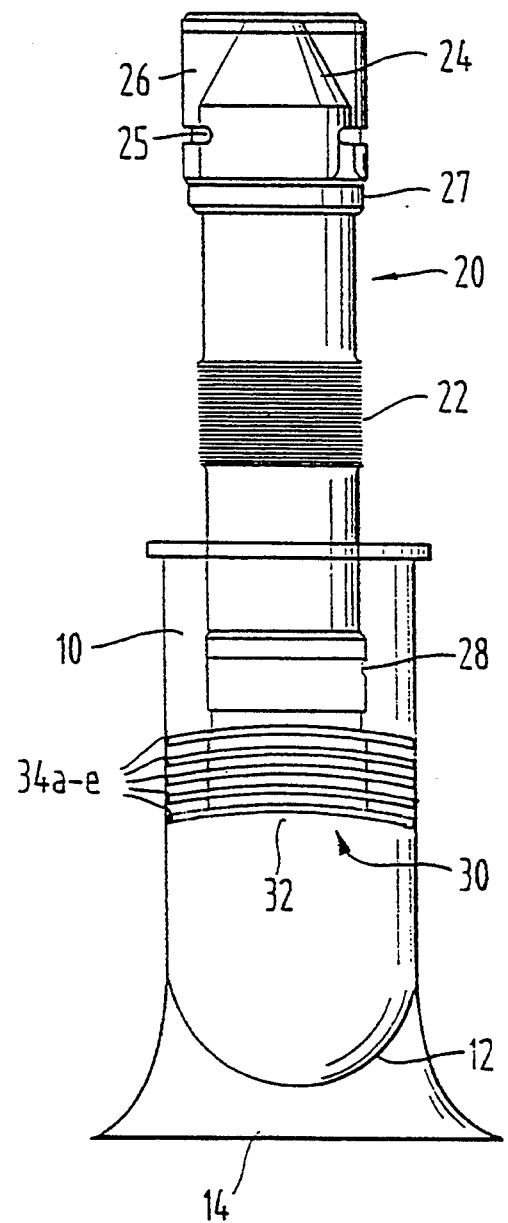
FIG. 1: an apparatus for mixing substances and filling the blended substances, such as bone cement, into an applicator.

The apparatus according to FIG. 1 comprises a tall, circular, cylindrical mixing bowl 10 having a round inner bottom 12 and a flat base 14.

The applicator 20 is formed as a syringe cartridge and has a corrugated gripping surface 22 and a conical front end 24 serving as a mouth piece for the application. A closure cap 26 is attached to this end by means of a bayonet closure 25 having a rising thread, said cap sitting close to a rib 27 on the applicator which serves as a stopper. On the other (during application rear) end of the vessel 20, a sealing means 30 is fastened by means of an adapter 28. The tubular body 32 of the sealing means 30 has in its interior a central opening and five flexible lamallae 34a–e at its perimeter. The sealing means 30 is made of teflon and the diameter of the lamallae gradually increases starting from the foremost lamella 34e which faces the bottom of the mixing bowl 10 and has the smallest diameter.

When mixing the bone cement, first the monomer and then the polymer powder is placed into the mixing bowl 10 and mixed; this will be explained in greater detail on the basis of FIGS. 2 to 4. Then the applicator 20 with its mounted sealing means 30, as shown in FIG. 1, is pushed from above into the mixing bowl 10 the top of which is open. When doing this the lamellae then adapt themselves to the shape of the rounded inner bottom 12 of the mixing bowl 10 and all of the bone cement is forced through the central opening of the sealing means 30 into the vessel 20. The lamellae 34 are designed in such a way that the air above the bone cement and/or the gases which escape during polymerisation can escape past the lamellae 34, but that, if at all, the bone cement can only pass by a certain number of the lamellae. The graduated diameter of the lamellae 34 assures that the bone cement cannot pass through all the lamellae even if one allows for a certain process tolerance range.

Once all the bone cement has been filled into the vessel 20 in this way, the adapter 28 with the sealing means 30 is removed from the vessel 20 and the vessel 20 is mounted onto a bone cement syringe such as the bone cement pistol according to EP-A1-170 120. Thus the applicator 20 serves directly as a cartridge for the application of the bone cement.

Figure 2:
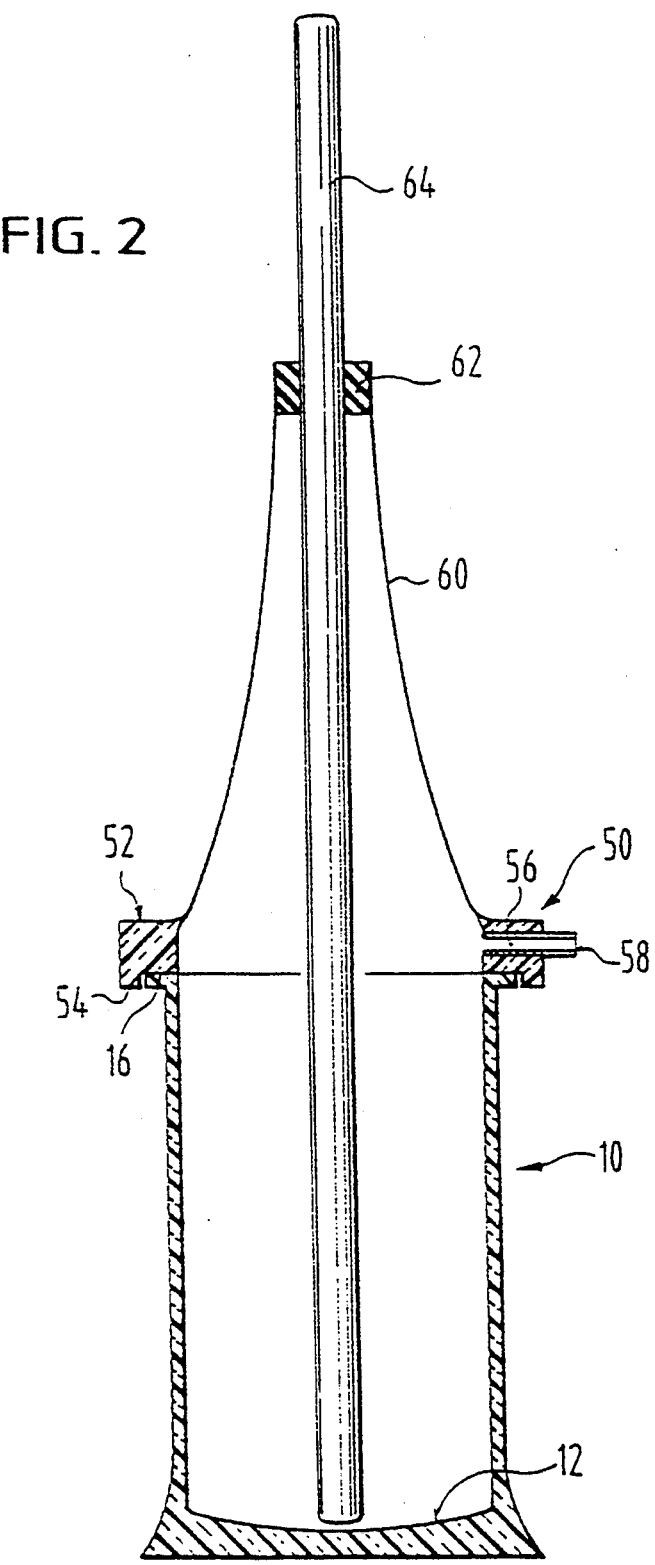
FIG. 2: a cross section of an embodiment of a mixing vessel with a tent-like vacuum lid and a cylindrical rod.

The mixing bowl 10 according to FIG. 2 basically corresponds to the mixing bowl according to FIG. 1 and has a concave inner bottom 12 and a surface ground upper rim 16. In order to enable stirring and mixing under vacuum, the mixing bowl 10 according to FIG. 2 comprises a vacuum lid 50, the firm rim 52 of which lies on the surface ground rim 16 of the mixing bowl 10. A silicon layer can be used to sealingly connect the two surfaces of the rim 16 and 52 which contact, but it is also possible to provide a sealing ring in a groove of the rim 16. The outer portion of the rim 52 of the lid 50 has a nose 54 which overlaps the rim 16 and prevents the lid 50 from being displaced relative to the rim 16 of the mixing bowl 10.

Furthermore, the rim 52 of the lid 50 is provided with a feed-through 56 and a connecting means 58 for connecting a vacuum lead (not illustrated), which leads to a pump which is not illustrated either.

In addition to the firm rim 52, the lid 50 has a flexible, tent-like inner portion 60. In the illustrated embodiment, the inner portion 60 is integrally connected to the rim 52 and is made of the same material as the rim 52, but is a continuation thereof and is thinner so that the material of the inner portion 60 exhibits a certain flexibility. Teflon and poly(4-methyl-1-pentene) are especially suitable materials therefor. However, the flexible inner portion 60 can also be connected to the firm rim 52 by means of a vacuum-tight connection such as a flanged joint and can be made of a different material than the firm rim 52, such as a stable plastic film.

An annular feed-through or passage 62 made of an expandable material, preferably sterilizable rubber or silicon, is welded in a vacuum-tight manner to the upper end of the roof-shaped or tent-like inner portion 60. The inner portion 60 with its feed-through 62 can be preloaded so that it will possess a certain stability. A round rod 64 runs through the flexible feed-through 62, said rod preferably being made of or coated with teflon and being about 8 mm thick.

The apparatus according to FIG. 2 is used to stir or premix the raw mixture of monomer and polymer powder in the mixing bowl 10 under vacuum in about the first 30 seconds of the mixing phase. As the inner portion 60 of the lid 50 is flexible, the round rod 64 is radially movable within the mixing bowl 10 and can also be guided along the inner side wall of the mixing bowl 10. For this purpose, it is important that the lid 50 does not protrude radially or inwardly over the inner wall of the mixing bowl 10. The round rod is used in order to prevent the cement from sticking to the rod during stirring and when later removing the rod and to prevent the mixture from rupturing, but to produce a laminar flow of the individual layers of the mixture, by means of which the process of blending is promoted.

Once the stirring and mixing phase has been completed, the round rod 64 is removed and the lid 50 is detached from the mixing bowl 10. The bone cement, as explained in connection with FIG. 1, can then be extruded into the applicator.

Figure 3:
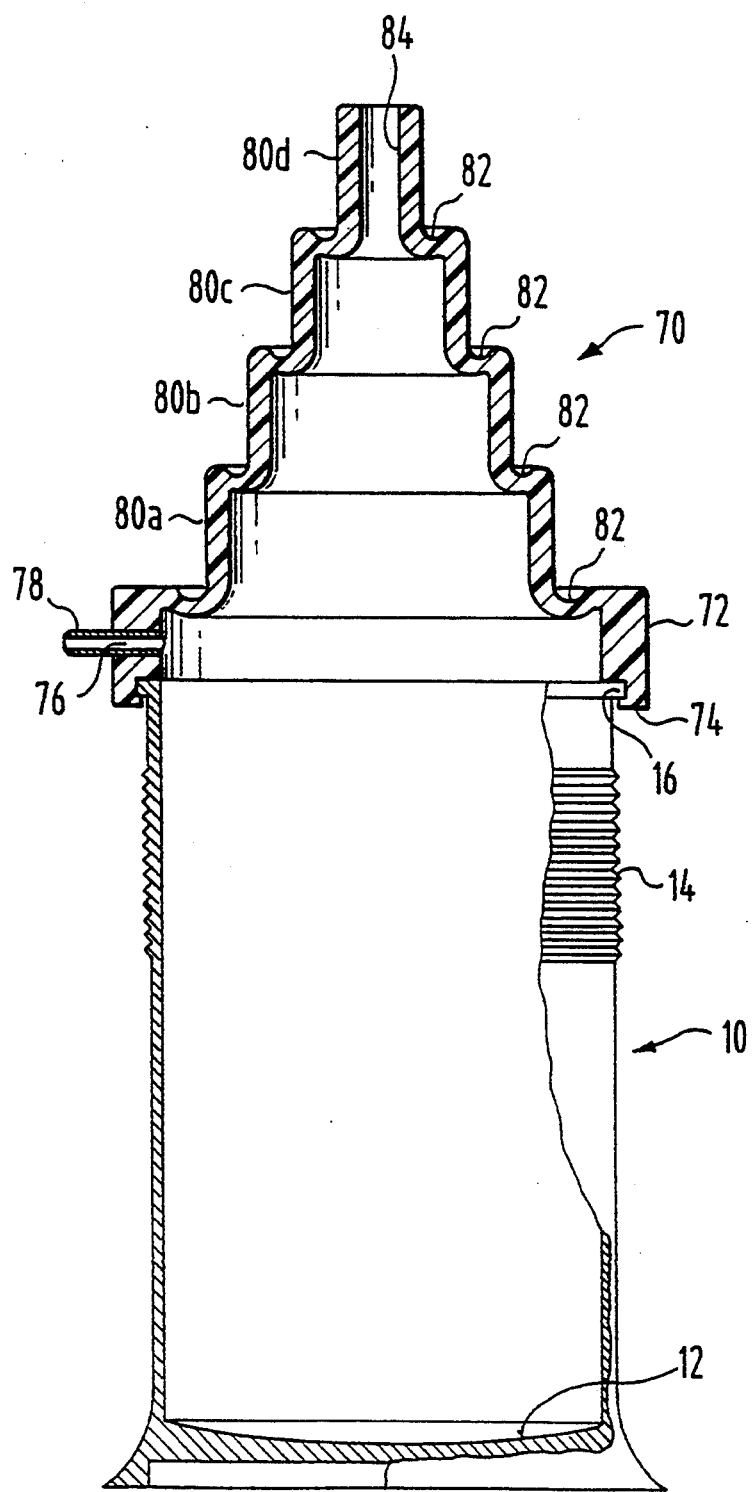
FIG. 3: a further embodiment of a mixing vessel with a tapered vacuum lid in the form of bellows shown in cross section.

FIG. 3 shows a further embodiment of a vacuum lid or cap 70 for the mixing bowl 10 in a cross sectional view, part of the mixing bowl 10 being shown in view.

The mixing bowl 10 according to FIG. 3 corresponds to the mixing bowl 10 according to FIG. 2, with FIG. 3 showing the provision of a corrugated gripping surface 14.

The vacuum lid 70 is integral and its shape comparable to that of taper-shaped bellows. The lid 70 consists of several connected portions, the diameter of which gradually decreases. The bottommost portion 72 is thicker than the other portions and serves as a rim which is mounted on the rim 16 of the mixing bowl in a vacuum-tight manner. For this purpose the portion 72 exhibits a nose 74 which firmly encompasses the rim 16 of the mixing bowl in the form of an undercut. Due to the elasticity of the material, the rim 72 can easily be pushed outwards to mount it on the mixing bowl 10.

Furthermore, the bottommost portion 72 is provided with a feed-through 76 for a (schematically shown) connection piece 78 for connecting a vacuum lead which leads to a pump.

In addition to the bottommost portion 72, the vacuum lid 70 according to FIG. 3 comprises four further portions 80a–d, the diameter of which gradually decreases, and which are integrally connected by slightly thinned, arched transition pieces 82. The effect of this construction is that the vacuum lid is relatively rigid in its axial direction and can hardly be axially compressed under vacuum, but the lid can be moved relatively easily or is mobile in the radial direction, especially the uppermost portion 80d thereof, the inner perimeter of which is a feed-through or passage 84 for the mixing rod (not shown in FIG. 3). The inner diameter of the feed-through 84 is preferably slightly smaller than the outer diameter of the mixing rod so that when the mixing rod is inserted, the feed-through 84 slightly expands and holds the inserted mixing rod in an essentially vacuum-tight manner.

In FIG. 3 the individual portions 80a–d are essentially circular and cylindrical in shape and all have the same wall thickness. However, the portions 80 can also be conical in shape and tapered as they go up, and the thickness thereof can optionally continuously decrease from the bottommost portion 80a to the uppermost portion 80d. Optionally, the transition pieces 82 can also have the same thickness as the portions 80 provided that the chosen material ensures that the entire lid 70 has sufficient lateral elasticity.

In all, the lid 70 should be elastic enough to let the uppermost portion 80d be radially moved to such an extent that the mixing rod, which is inserted through the feed-through 84, lies parallel to the inner wall surface of the mixing bowl 10 and can be moved along this surface.

As shown in FIG. 3, the spring-like transition pieces 82 can be U-shaped. Optionally they can be straight and at right angles to each of the portions 80.

Figure 4:
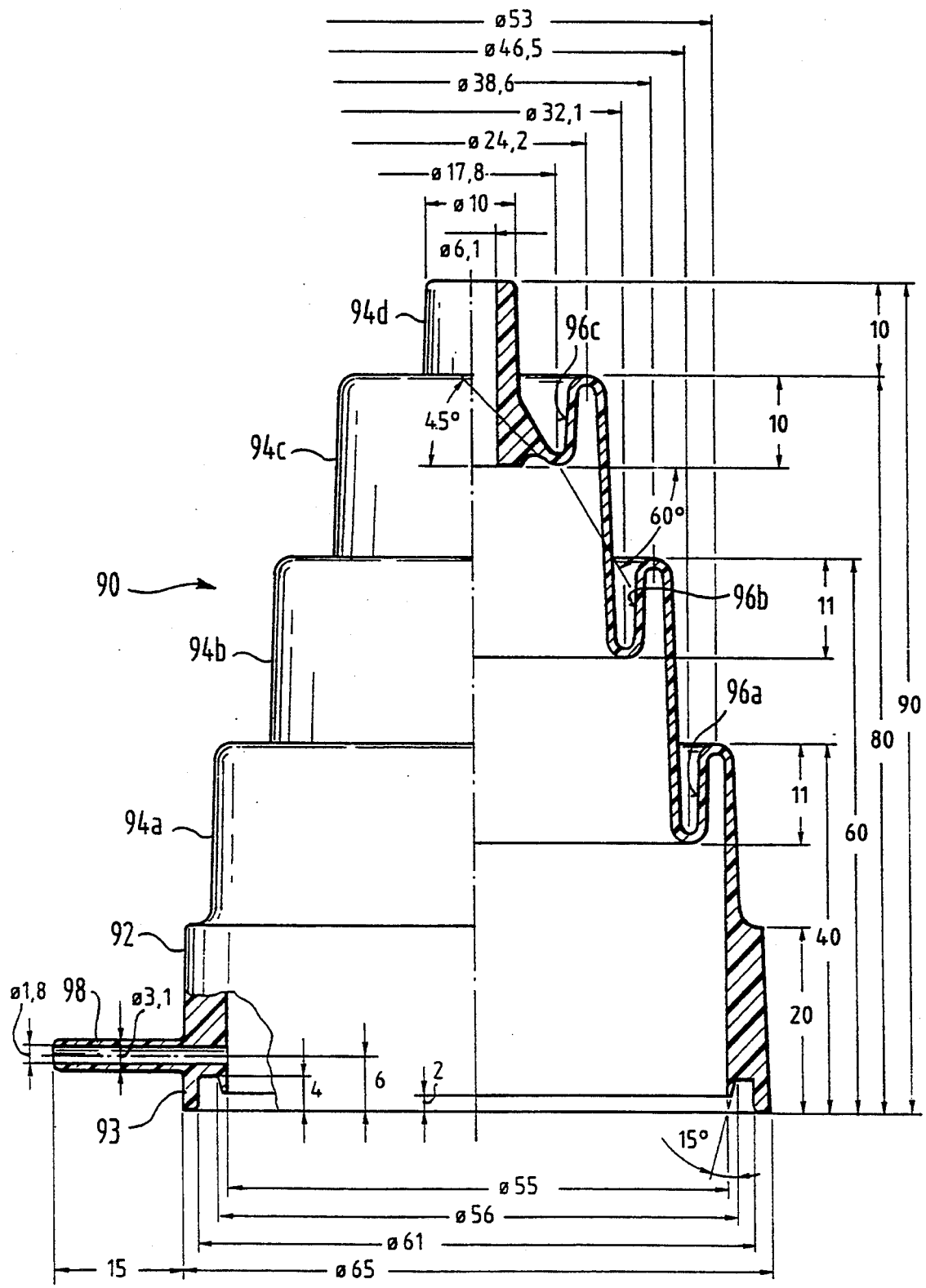
FIG. 4: a further embodiment (to scale) of a bellow-shaped vacuum lid in a partial section.

FIG. 4 shows a further embodiment of the bellow-shaped vacuum lid which is essentially to scale and partially in cross section. The numbers in FIG. 4 mean "mm" if not defined otherwise.

The vacuum lid 90 according to FIG. 4 comprises a solid bottommost portion 92 which serves as a rim at the same time. The projection 93 of said portion encompasses the upper rim of the mixing bowl, and said portions connects the vacuum lid 90 to the mixing bowl (only outlined in FIG. 4) in a vacuum-tight manner.

The bottommost portion 92 tapers as it goes up to the next portion 94a which essentially extends in the axial direction, as is the case in portion 92. The further portions 94b and 94c are of essentially the same thickness as portion 94a and are slightly conical and inclined in an inward direction. Loop-shaped transition pieces 96a, 96b and 96c are provided between each of the portions of the vacuum lid 90 and have a double U shape and are of the same thickness as the middle portions of the vacuum lid 90. The uppermost transition piece 96c thickens towards the end and merges into the equally thickened uppermost portion 94d of the vacuum lid 90, the inner perimeter of which forms the holding means or feed-through for a round mixing rod (not shown in FIG. 4).

The upper surface of the thickened portion of the transition piece 96c is inclined at an angle of about 30° to the axial direction, and the lower surface thereof is inclined at an angle of about 45°. This is of special advantage for the flexibility of the feed-through for the mixing rod. On the whole the vacuum lid 90 and its meander-shaped cross section are extraordinarily flexible which means that the mixing rod can still be easily moved to stir the bone cement when under vacuum. As regards the flexibility of the vacuum lid 90, its extended, loop-shaped cross section together with the properties of material it is made of are especially advantageous. The material used for the vacuum lid 90 is preferably Hytrel ® or Santoprene ®.

The bottommost portion 92 of the vacuum lid 90 is integrally provided with a connecting piece 98 for a vacuum lead.

The invention is not limited to the above examples which relate to mixing bone cement and filling it into an applicator, but can be generally used to blend a mixture consisting of at least two components and to fill the blended mixture into a vessel or container. The aforementioned examples of the apparatus according to the invention can therefore be generally applied in stirring and mixing substances and filling them into a vessel.

I claim:

1. A mixing apparatus comprising a mixing bowl having a generally vertical, longitudinal axis and a lid for sealing the mixing bowl in a vacuum-tight manner, said lid comprises a passage therethrough for a mixing rod, said passage defining a generally verticle axis, wherein the lid is configured to restrict motion of the passage in the axial direction of the mixing bowl, the lid being relatively rigid in the axial direction of the mixing bowl against a vacuum established within the mixing bowl while allowing radial movement of the passage relative to the axis of the mixing bowl.

2. The mixing apparatus according to claim 1, wherein the lid comprises a firm rim and an inner portion which is flexible in the radial direction and comprises the passage for the mixing rod.

3. The mixing apparatus according to claim 1, wherein the lid comprises a plurality of individual portions in the axial direction, each having a diameter, the diameter of each portion being smaller than the diameter of the portion beneath it, and the individual portions are connected to one another by means of flexible transition pieces (82; 96).

4. The mixing apparatus according to claim 3, wherein the portions and transition pieces are integrately connected to one another.

5. The mixing apparatus according to claim 1, wherein the lid is made of a sterilisable material.

6. The mixing apparatus according to claim 5, wherein the material is a polyester elastomer.

7. The mixing apparatus according to claim 1, wherein the lid comprises a connection piece for connecting a vacuum lead.

8. The mixing apparatus according to claim 1, wherein the mixing rod is a round rod.

9. The mixing apparatus according to claim 1, wherein the mixing bowl is cylindrical and the inner bottom thereof is concave or rounded.

10. The mixing apparatus according to claim 1, wherein the lid is bellow-shaped and tapers upwardly.

* * * * *